United States Patent [19]

Nettles, Jr. et al.

[11] Patent Number: 4,484,539

[45] Date of Patent: Nov. 27, 1984

[54] OVIPOSITIONAL STIMULANT FOR TRICHOGRAMMA SPP.

[75] Inventors: William C. Nettles, Jr.; Richard K. Morrison, both of College Station, Tex.; Zhong-Neng Xie, Guangzhou, China; Debra Ball, Bryan, Tex.; Cyndy A. Shenkir, College Station, Tex.; S. Bradleigh Vinson, Bryan, Tex.

[73] Assignee: The United States of America as represented by the Secretary of Agriculture, Washington, D.C.

[21] Appl. No.: 532,431

[22] Filed: Sep. 15, 1983

[51] Int. Cl.$^3$ .............................................. A01K 67/00
[52] U.S. Cl. ...................................................... 119/1
[58] Field of Search ........................................... 119/1

[56] References Cited

U.S. PATENT DOCUMENTS

| | | | |
|---|---|---|---|
| 3,893,420 | 7/1975 | Andreev et al. | 119/1 |
| 3,941,089 | 3/1976 | Andreev et al. | 119/1 |
| 4,370,946 | 2/1983 | Voegele et al. | 119/1 |
| 4,418,647 | 12/1983 | Hoffman | 119/1 |

OTHER PUBLICATIONS

G. F. Rajendram and K. S. Hagen, "Trichogramma Oviposition into Artificial Substrates", Environ. Entomol., 3:399–401, (1974).

G. F. Rajendram, "Some Factors Affecting Oviposition of *Trichogramma Californicum*, (Hymenoptera: Trichogrammatidae) in Artificial Media", *Can. Entomol.*, 110:345–352, (1978).

J. David Hoffman et al., "In Vitro Rearing of the Endoparasitic Wasp, *Trichogramma pretiosum*", *Annals Entolological Society America*, 68:335–336, (1975).

*Primary Examiner*—Hugh R. Chamblee
*Attorney, Agent, or Firm*—M. Howard Silverstein; David G. McConnell; Raymond C. Von Bodungen

[57] ABSTRACT

$K^+$, $Mg^{2+}$, and $SO_4^{2-}$ were important components eliciting oviposition by *Trichogramma pretiosum* Riley in aqueous solutions in artificial wax eggs. $Ca^{2+}$ inhibited oviposition in a $KCl$-$MgSO_4$ solution. The solutions most active in stimulating oviposition were 124.7-36.5 and 83.1-24.3 mM, respectively, of $KCl$-$MgSO_4$.

3 Claims, No Drawings

OVIPOSITIONAL STIMULANT FOR TRICHOGRAMMA SPP.

BACKGROUND OF THE INVENTION (1) Field of the Invention

This invention relates to a process for using chemicals to stimulate oviposition in insects.

(2) Description of the Prior Art

Insecticides are not always effective or desirable for the control of many species of insects which cause enormous losses of food and fiber. Egg parasitoids of the genus Trichogramma are especially promising biocontrol agents because: (1) they parasitize a wide range of host insects, (2) they destroy the host in the egg so that no larval feeding damage occurs, (3) they are readily manipulated and mass-reared in the laboratory, and (4) host-seeking chemicals are available to enhance the effectiveness of released and indigenous parasitoids in the field. Trichogramma spp. are the most widely studied entomophagous insects and are used for biocontrol on global basis both in developed and developing countries. Augmentative releases of these parasitoids are restricted by the expense associated with the production of host eggs. Economical mass production of parasitoids on artificial diets in quantities suitable for augmentative releases requires techniques for the collection of large numbers of Trichogramma spp. eggs.

Eggs were first collected by dissecting them from parasitized host eggs. Next (Rajendram and Hagen, "Trichogramma Oviposition into Artificial Substrates" Environ. Entomol. 3:399–401 (1974)) reported that Neisenheimer's solution (a mixture composed mostly of NaCl and with much smaller amounts of $NaHCO_3$, $CaCl_2$, and KCl) stimulated oviposition by Trichogramma californicum. Results were poor and erratic. It is significant that Rajendram "Some Factors Affecting Oviposition of Trichogramma californicum (Hymenoptera:Trichogrammatidae) in Artificial Media" Can. Entomol. 110:345–352 (1978) concluded that "no particular salt, amino acid, or vitamin tested was seen to be essential for eliciting oviposition". Hoffman et al, Annals Entomological Society America, 68:335–6 (1975) used insect hemolymph to elicit oviposition and this also has been used by several Chinese workers. The Chinese also have used solutions of salts, amino acids, proteins, protein hydrolyzates, and artificial diets containing amino acids, salts, etc., but all appear to be weak ovipositional stimulants for Trichogramma. A mixture of either magnesium salts or trehalose and several amino acids stimulated oviposition by the parasite Itoplectis conquisitor.

SUMMARY OF THE INVENTION

A unique and valuable process for stimulating oviposition in insects is disclosed. Artificial wax eggs containing a salt solution with one or more ions selected from the group consisting of $K^+$, $Mg^{2+}$, $Cl^-$, and $SO^{2-}_4$ are fabricated. The concentration of the salt solution is critically designed to be sufficient to stimulate the insects. The insects are brought into contact with the artificial eggs for sufficient time and at sufficient temperature to allow the insects to oviposit their eggs into the salt solution as a result of the stimulus of the solution.

DESCRIPTION OF THE PREFERRED EMBODIMENTS

Trichogramma pretiosum was reared on eggs of the Angoumois grain moth Sitotroga cerealla (Olivier) (Morrison and Hoffman, "An Improved Method for Rearing The Angoumois Grain Moth", U.S. Dept. of Agric., Agric. Res. Serv. ARS-S-104, pp 5 (1976) and Morrison et al, "A Unified System for the Production and Preparation of Trichogramma pretiosum for Field Release", Southwest Entomol. 3:62–68 (1978)). The diet of the host larvae was wheat. The parasitoids were reared at 27° C. and 80% relative humidity except when pupae were cold programmed at 16°. Adults used in the tests emerged soon after the temperature was changed to 27°.

The pH of the test solutions was adjusted to 7.0 with either KOH or NaOH and all solutions contained 1.0 nM of either $KH_2PO_4$ or $NaH_2PO_4$. NaOH and $NaH_2PO_4$ were used when solutions contained $Na^+$ and no $K^+$.

Test solutions were encapsulated inside wax spheres by the method of K. S. Hagen and T. L. Tassan (1965) J. Economic Entomology 58:999–1000. The artificial eggs were prepared by placing a 2–3 mm thick layer of paraffin-petroleum jelly (3:1) on top of the test solution in a glass vial held at 65° C. The tip of a Pasteur capillary pipette was immersed in the liquid, removed, and touched to a glass slide (1.2×2.5 cm). The resulting egg had a diameter of about 2.5 mm. Each glass slide held three wax eggs, and a slide for each solution tested was placed inside a Petri dish (10×1.5 cm) that was modified by removal of the lid tabs to prevent the escape of the minute parasitoids. The sex ratio of the parasitoids was 1:1 and we usually used about 300–600 of the adult females in each dish. The number varied because counting these small insects precisely was difficult. We used larger numbers of parasitoids in tests in which the number of test solutions was larger than usual.

The Petri dishes containing the artificial eggs and Trichogramma were rotated at one rpm for 16 hours and the Trichogramma were allowed to contact the wax spheres and deposit eggs into the test solutions. Rotation was necessary to negate the strong positive phototactic behavior of these insects. Each test was conducted under either of two holding conditions. Usually about half was held at 27° C. and 80% relative humidity and the other half was exposed to 25° C. and 40% relative humidity. After breaking open the artificial eggs, visual counts of the Trichogramma eggs was made. Because of the variable number of parasitoids used in each dish, the results were expressed as percentages of the total number of eggs collected in the artificial eggs inside each petri dish. Within the range used there was no apparent effect from the number of parasitoids on the percentage distribution of eggs between test solutions. Holding conditions (temperature and reltive humidity) had no effect on percentage distribution of eggs, but the number of eggs deposited was reduced at the lower temperature and relative humidity.

The statistical method was a multiway classification using the chi-square test (Steel and Torrie, "Principles and Procedures of Statistics", McGraw-Hill, New York, pp. 384–386 (1960)).

EXPOSURE TIME

Females ovipositioned at least 10 eggs per female when the exposure period to artificial eggs was 4, 5, 6, or 18 hours.

TEMPERATURE

Oviposition at 27° C. and 25° C. averaged 2915 and 1720 eggs per dish. With natural host eggs oviposition occurs mainly between 21° and 32° C., but, can occur as high as 37° C.

The following experiments and resulting data demonstrate the preferred embodiments of the invention:

EXAMPLE 1

The Effects of pH on Oviposition by *T. pretiosum* were Average Number of Eggs

| pH | Test 1 | Test 2 | Test 3 | Test 4 | Test 5 | Test 6 |
|---|---|---|---|---|---|---|
| 6.50 | 436 | 1796 | | | | |
| 6.75 | 797 | | | | | |
| 7.00 | 624 | 402 | 739 | 844 | 759 | 447 |
| 7.25 | 758 | | | | | |
| 7.50 | 367 | | 4125 | | | |
| 8.00 | | | | 141 | | |
| 8.50 | | | | | 56 | |
| 9.00 | | | | | | 73 |

EXAMPLE 2

KCl Alone (without MgSO$_4$) was a Relatively Weak Ovipositional Stimulant for *T. pretiosum*:

| mM KCl | Average Number of Eggs |
|---|---|
| 5.2 | 1 |
| 10.4 | 3 |
| 20.8 | 10 |
| 41.6 | 9 |
| 83.1 | 51 |
| 166 | 43 |
| 322 | 1 |

EXAMPLE 3

The following demonstrates conclusively that a synergistic effect exists when KCl and MgSO$_4$ are used to stimulate *T. pretiosum* rather than when used alone.

Synergistic Effect—For *Trichogramma pretiosum* KCl was the stimulant and MgSO$_4$ was the synergist. For *T. minutum* both KCl and MgSO$_4$ were about equally active as stimulants. The combination of KCl—MgSO$_4$ was 49 and 6 times more active for *T. pretiosum* and *T. minutum*, respectively, than was the total of each salt alone.

| | Average Number of Eggs | |
|---|---|---|
| | *T. pretiosum* | *T. minutum* |
| 83.1 mM KCl - 24.3 mM Mg SO$_4$ | 3024 | 1392 |
| 83.1 mM KCl | 59 | 100 |
| 24.3 mM MgSO$_4$ | 3 | 119 |

EXAMPLE 4

Additional evidence that a mixture of KCl—MgSO$_4$ was the most active stimulant for *T. pretiosum* when compared to other discovered stimulants.

| | Average Number of Tests | |
|---|---|---|
| | Test 1 | Test 2 |
| 83.1 mM KCl - 24.3 mM MgSO$_4$ | 1922 | 2067 |
| 41.6 mM K$_2$SO$_4$ - 24.3 mM MgCl$_2$ | 802 | 912 |
| 83.1 mM KCl - 24.3 mM MgCl$_2$ | 562 | |
| 41.6 mM K$_2$SO$_4$ - 24.3 mM MgSO$_4$ | 365 | |

This demonstrates that K$^+$, Mg$^{2+}$, Cl$^-$, and SO$_4^{2-}$ all enhance oviposition.

Additional evidence that Mg$^{2+}$ is an important component of the ovipositional stimulant for *T. pretiosum* is provided by this experiment:

| mM KCl | mM K$_2$SO$_4$ | mM MgSO$_4$ | Average Number of Eggs |
|---|---|---|---|
| 83.1 | | 24.3 | 1067 |
| 41.6 | 20.8 | | 40 |

Oviposition was very weak when Mg$^{2+}$ was absent from a mixture of K$^+$, Cl$^-$, and SO$_4^{2-}$.

CONCENTRATION EFFECTS ("NO CHOICE") TESTS) EXAMPLES 5 AND 6

These experiments were performed so that the *T. pretiosum* females were exposed either to a single salt mixture ("no choice" tests) or to several different salt solutions ("preference" tests).

EXAMPLE 5

When the KCl concentration was held constant at 83.1 mM and the MgSO$_4$ concentration varied from 0.0 to 48.5 mM, oviposition was strong down to relatively low concentrations of MgSO$_4$:

| | | Average Number of Eggs | |
|---|---|---|---|
| mM KCl | mM MgSO$_4$ | Test 1 | Test 2 |
| 83.1 | 48.5 | 2561 | |
| 83.1 | 36.4 | 2711 | |
| 83.1 | 18.2 | 2969 | |
| 83.1 | 12.1 | 2348 | |
| 83.1 | 9.1 | 2625 | |
| 83.1 | 6.1 | 2897 | |
| 83.1 | 4.5 | 2258 | |
| 83.1 | 3.03 | 2538 | |
| 83.1 | 1.53 | | 1144 |
| 83.1 | 0.76 | | 1334 |
| 83.1 | 0.38 | | 847 |
| 83.1 | 0.19 | | 887 |
| 83.1 | 0.090 | | 520 |
| 83.1 | 0.047 | | 786 |
| 83.1 | 0.024 | | 478 |
| 83.1 | 0.012 | | 415 |
| 83.1 | 0.0 | | 361 |

EXAMPLE 6

When the MgSO$_4$ concentration was held constant at 6.1 mM and the KCl concentration varied between 99.7 and and 664.8 mM, oviposition by *T. pretiosum* was very weak at the two highest KCl concentrations:

| mM KCl | mM MgSO$_4$ | Average Number of Eggs |
|---|---|---|
| 99.7 | 6.1 | 1850 |
| 116.34 | 6.1 | 1968 |
| 124.65 | 6.1 | 2366 |
| 132.96 | 6.1 | 1635 |
| 149.58 | 6.1 | 1508 |

-continued

| mM KCl | mM MgSO$_4$ | Average Number of Eggs |
|---|---|---|
| 166.2 | 6.1 | 1070 |
| 332.4 | 6.1 | 26 |
| 664.8 | 6.1 | 0 |

CONCENTRATION EFFECTS ("PREFERRED TESTS") EXAMPLES 7 THRU 9

EXAMPLE 7

When the KCl concentration was held constant at 83.1 mM and the MgSO$_4$ concentration was varied between 6.1 and 388.8 mM, oviposition occurred in all solutions:

| mM KCl | mM MgSO$_4$ | Average Number of Eggs |
|---|---|---|
| 83.1 | 6.1 | 90 |
| 83.1 | 12.2 | 220 |
| 83.1 | 24.3 | 170 |
| 83.1 | 48.6 | 1457 |
| 83.1 | 97.2 | 806 |
| 83.1 | 194.4 | 236 |
| 83.1 | 388.8 | 96 |

EXAMPLE 8

When the KCl concentration was constant at 83.1 mM and MgCl$_2$ concentration varied from 6.1 and 388.8 mM, oviposition occurred in all solutions except those with the highest MgCl$_2$ concentrations:

| mM KCl | mM MgCL$_2$ | Average Number of Eggs |
|---|---|---|
| 83.1 | 6.1 | 176 |
| 83.1 | 12.2 | 173 |
| 83.1 | 24.3 | 630 |
| 83.1 | 48.6 | 1191 |
| 83.1 | 97.2 | 114 |
| 83.1 | 194.4 | 0 |
| 83.1 | 388.8 | 0 |

EXAMPLE 9

When the MgSO$_4$ concentration was constant at 24.3 mM and the KCl concentration varied from 49.9 to 166.22 mM, eggs were deposited by *T. pretiosum* females in all solutions:

| mM KCl | mM MgSO$_4$ | Average Number of Eggs Test 1 | Test 2 |
|---|---|---|---|
| 49.9 | 24.3 | 16 | 32 |
| 66.5 | 24.3 | 280 | |
| 74.8 | 24.3 | 342 | |
| 83.1 | 24.3 | 1853 | 1217 |
| 91.4 | 24.3 | 1074 | |
| 99.7 | 24.3 | 794 | |
| 116.3 | 24.3 | 887 | 1489 |
| 133.0 | 24.3 | 1074 | |
| 149.0 | 24.3 | 1084 | 1319 |
| 166.2 | 24.3 | 257 | |

EXAMPLE 10

When the ratio of KCl to MgSO$_4$ was constant and varied from 5.2–1.5 to 664.8–194.4 mM, significant oviposition occurred in four solutions:

| mM KCl | mM MgSO$_4$ | Average Number of Eggs Test 1 | Test 2 |
|---|---|---|---|
| 5.2 | 1.5 | 0 | |
| 10.4 | 3.0 | 0 | |
| 20.8 | 6.1 | 0 | |
| 41.6 | 12.2 | Trace | |
| 62.3 | 18.2 | 34 | 6 |
| 83.1 | 24.3 | 187 | 91 |
| 124.7 | 36.5 | 476 | 187 |
| 166.2 | 48.6 | 170 | 79 |
| 332.4 | 97.2 | 0 | |
| 664.8 | 194.4 | 0 | |

EXAMPLE 11

When salt solutions were formulated to equal the K$^+$, Na$^+$, Mg$^{2+}$, and Ca$^{2+}$ concentrations of *Heliothis* spp. and *Sitotroga cerealella*, oviposition occurred in all samples but was highest in those solutions containing 81.4–83.1 mM KCl—21.8–24.3 mM MgSO$_4$:

| mM KCl | mM MgSO$_4$ | mM NaCl | mM CaCl$_2$ | Average Number of Eggs |
|---|---|---|---|---|
| 24.0 | 35.0 | 9.0 | | 1 |
| 37.0 | 68.0 | 23.0 | | 1 |
| 48.5 | 12.5 | 17.0 | | 44 |
| 42.6 | 18.9 | 43.0 | | 73 |
| 81.4 | 21.8 | 4.9 | | 1016 |
| 83.1 | 24.3 | 8.3 | | 774 |
| 83.1 | 24.3 | 8.3 | 9.0 | 513 |

In summary, the data demonstrate that a rather wide range of concentrations of KCl—K$_2$SO$_4$—MgSO$_4$—MgCl$_2$ solutions stimulate oviposition by *T. pretiosum*.

K$^+$, Mg$^{2+}$, Cl$^-$, and SO$_4^{2-}$ are important components of the ovipositional stimulant for *T. pretiosum* and Na$^+$, Mn$^{2+}$, Fe$^{3+}$, Zn$^{2+}$, and Cu$^{2+}$ do little or nothing to enhance oviposition. Ca$^{2+}$ inhibits oviposition. Apparently K$^+$ is an ovipositional stimulant and Mg$^{2+}$ is a synergist for *T. pretiosum* because the parasitoids oviposited mainly into KCl solutions (but rather weakly compared to the KCl—MgSO$_4$ controls), very weakly into NaCl solutions, and extremely weakly into MgSO$_4$ solutions. For *T. minutum* the synergistic effect of Mg was not as obvious because MgSO$_4$ alone was about as active as KCl alone as an ovipositional stimulant and the synergistic effect of the KCl—MgSO$_4$ combination was not as great as it was for *T. pretiosum*.

Most of the ovipositional activity of KCl occurred in about the same concentration range regardless of whether the test solution was KCl alone (21–166 mM), KCl—MgSO$_4$ with MgSO$_4$ constant at 24.3 mM (66–150 mM), or a constant ratio of KCl—MgSO$_4$, (83–166 mM KCl).

Because of the rather similar chemical properties of calcium and magnesium, it is rather remarkable that Mg$^{2+}$ synergized the ovipositional activity of K$^+$ and that Ca$^{2+}$ inhibited oviposition.

We claim:
1. A process for stimulating oviposition in *Trichogramma pretiosum* insects comprising:
    (a) fabricating an artificial wax egg containing salt solution of KCl and MgSO$_4$, said solution of sufficient concentration to stimulate the insect;
    (b) allowing the insects to come into contact with the artificial wax eggs for sufficient time and at sufficient temperature to allow the insects to oviposit their eggs into the solution as a result of solution stimulus.
2. The process of claim 1 wherein the temperature is from about 22° C. to 37° C.
3. The process of claim 1 wherein the salt solution is from about 48–116 mM KCl and from about 12–389 mM MgSO$_4$.

* * * * *